US00PP17356P2

(12) United States Plant Patent
Doguet et al.

(10) Patent No.: US PP17,356 P2
(45) Date of Patent: Jan. 16, 2007

(54) BUFFALOGRASS PLANT NAMED 'DENSITY'

(50) Latin Name: *Buchloe dactyloides (Nutt) Engelm*
Varietal Denomination: Density

(76) Inventors: David Doguet, 1602 Continental, Pleasanton, TX (US) 78064; Virginia Lehman, 811 Mountain River Dr., Lebanon, OR (US) 97355

( * ) Notice: Subject to any disclaimer, the term of this patent is extended or adjusted under 35 U.S.C. 154(b) by 60 days.

(21) Appl. No.: 11/331,602

(22) Filed: Jan. 17, 2006

(51) Int. Cl.
*A01H 5/00* (2006.01)

(52) U.S. Cl. ..... Plt./391
(58) Field of Classification Search ..... Plt./391
See application file for complete search history.

(56) References Cited

U.S. PATENT DOCUMENTS

| | | | | | |
|---|---|---|---|---|---|
| PP7,539 | P | * | 5/1991 | Engelke et al. | Plt./391 |
| PP8,475 | P | * | 11/1993 | Riordan et al. | Plt./391 |
| PP11,004 | P | * | 7/1999 | Doguet | Plt./391 |
| PP11,373 | P | * | 5/2000 | Riordan et al. | Plt./391 |
| PP12,910 | P2 | * | 9/2002 | Wu et al. | Plt./391 |

* cited by examiner

*Primary Examiner*—Anne Marie Grunberg
*Assistant Examiner*—Annette H Para

(57) ABSTRACT

An asexually reproduced variety of female perennial buffalograss distinguished by a unique combination of characters including female inflorescence, shorter plant canopy, and shorter stolon internode lengths.

2 Drawing Sheets

Latin name of the genus and species of the plant claimed: The present invention relates to the genus and species *Buchloe dactyloides* (*Nutt*) *Engelm.*
Variety denomination: 'Density'.

BACKGROUND OF THE INVENTION

Field of Invention

The present invention relates to a new and distinct asexually reproduced variety of perennial *Buchloe dactyloides* (*Nutt*) *Engelm.*

BRIEF SUMMARY OF THE INVENTION

Background of the Invention

This invention relates to a new and distinct perennial female buffalograss cultivar identified as 'Density' buffalograss (herein referred to as 'Density'). The inventors, David Doguet and Virginia G. Lehman, discovered 'Density' under cultivated conditions in a mowed roadside lawn area near Houston, Tex. 'Density' was identified as a distinctly different vegetative female patch or segregated clonal plant differing by higher tiller density than the surrounding male or female clones. The inventors asexually reproduced 'Density' by taking vegetative cuttings of the plant material from the roadside, including stolons and tillers, cutting the stolons into segments, each with a vegetative bud, and rooting them in field nurseries at Bladerunner Farms, Inc. nurseries near Poteet, Tex. Stolons and vegetative plugs of Density were asexually reproduced, moved to the greenhouse and field nurseries, near Lebanon, Oreg. with further asexual reproduction for further evaluation and testing.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Buffalograss plant named 'Density'.

BRIEF DESCRIPTIONS OF THE ILLUSTRATIONS

Figure 1:
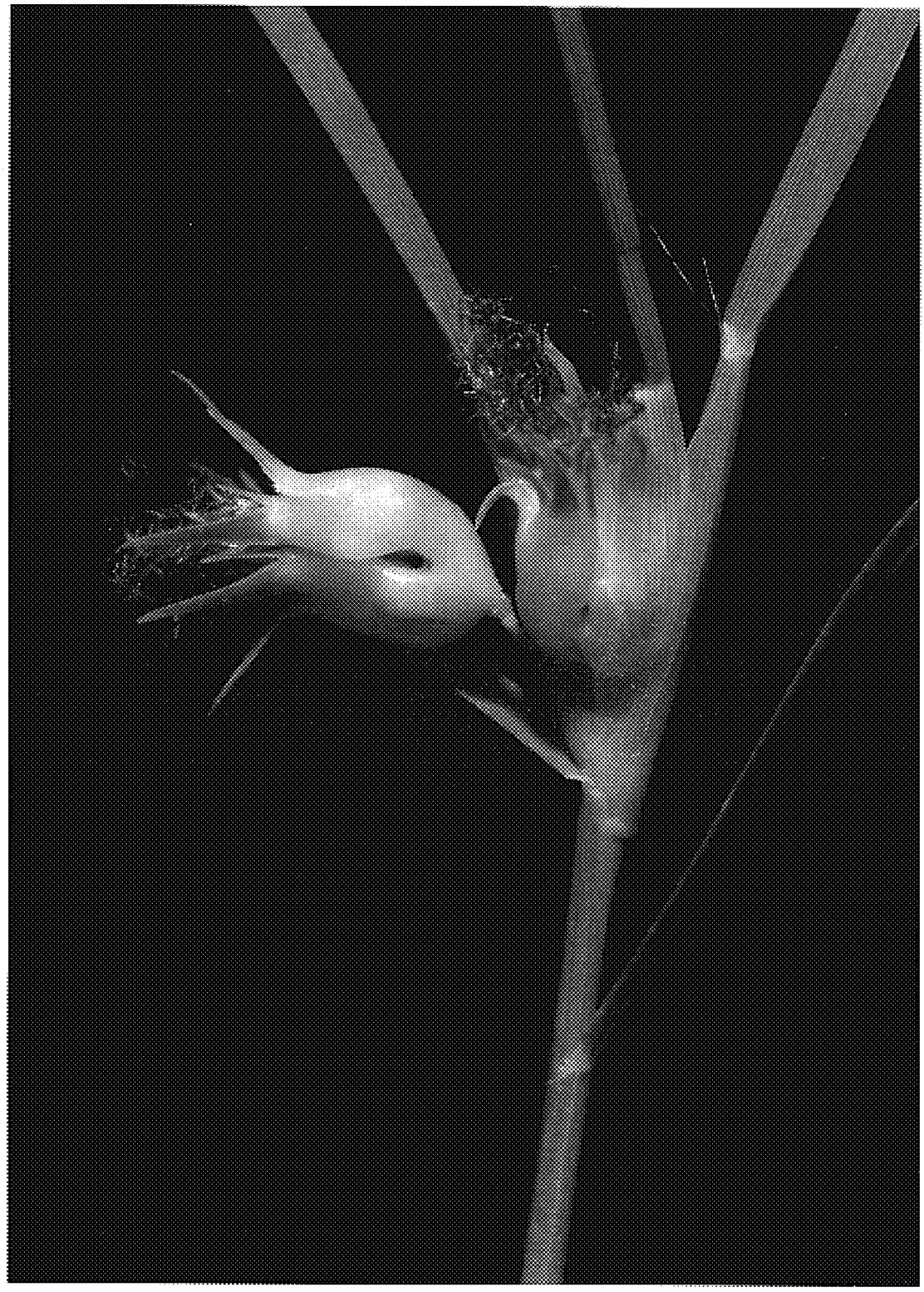

FIG. 1. Inflorescence of 'Density' buffalograss.

Figure 2:
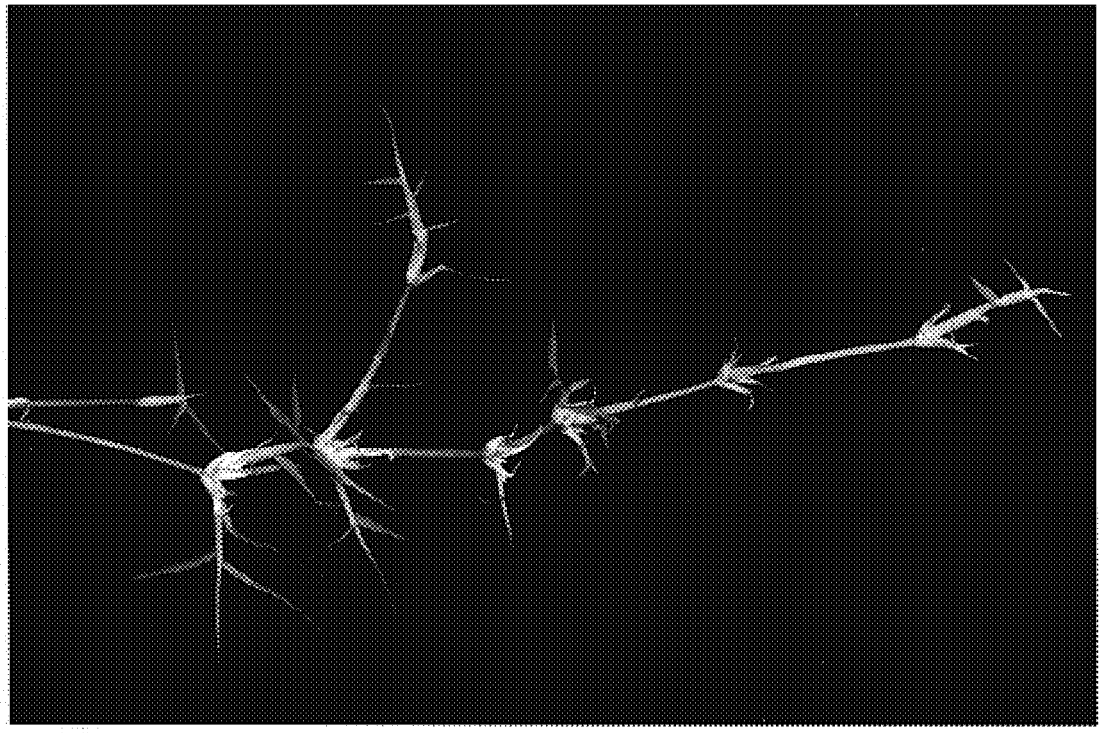

FIG. 2. Stolon of 'Density' buffalograss.

COMPLETE DESCRIPTION OF THE VARIETY

'Density' was characterized in greenhouse and field conditions. 'Density' is a unique female or pistilate variety of buffalograss (*Buchloe dactyloides* (*Nutt*) *Engelm.*) that was discovered under cultivated conditions in a mowed roadside area near Houston, Tex. 'Density' was identified as having a much higher tiller density than the surrounding male or female buffalograss clones. The mowed roadside areas was located in USDA Plant Hardiness Zone 9a. 'Density' was propagated by the inventors under field and greenhouse conditions in Poteet, Tex. and Lebanon, Oreg. by cutting of stolons, rooting them in soil, and planting of the rooted material to provide planting stock for studying performance and for comparison of morphological characters after propagation. 'Density' has been propagated by stolons, tillers, and sod. Asexually reproduced plants of 'Density' have remained stable and true to type through successive generations of propagation. 'Density' produces pistilate or female inflorescences, but no seedlings have been noted from 'Density'.

'Density' is a perennial buffalograss that spreads by stolons and tillers. Characteristics of 'Density' measured in 2005 were taken from plants that were approximately 15 months in age. The greenhouse was located near Lebanon, Oreg., with a nighttime low temperature of 50 degrees F., and daytime high of 80 degrees F., and a minimum soil temperature of 77 degrees F. The plants were grown with a minimum 14-hour day length, supplemented with photosynthetically active radiation equivalent to approximately 50% sunlight. The plants were fertilized with the equivalent of 1 pound of actual N per month, using a soluble fertilizer of 20-20-20 in two equal soluble applications per month.

'Density' has a shorter canopy height than '609' U.S. Plant Pat. No. 8,475 (Table 1) when measured under greenhouse conditions in Lebanon, Oreg., 2005. 'Density' has shorter internode lengths (Table 2), providing a higher density turfgrass. As a dioecious pistilate or female clone, no burrs with viable seeds of 'Density' have developed; no seedlings have been noted in field production area or field test areas. 'Density' has retained the unique characters during successive stages of propagation and has shown to be a stable variety in asexual propagation.

'Density' has not shown susceptibility to the buffalograss mite [*Eriophyes slykhuisi* (Hall)] in tests to date in the Poteet, Tex. nor Lebanon, Oreg. site. In addition, 'Density' has not shown susceptibility to any diseases or other insects common to the buffalograss genus such as mealybug. 'Density' shows shorter internode lengths than 'Prairie' or '609', and when harvested as sod, maintains sod block integrity. 'Density' is adapted North/South from the Kansas-Oklahoma border through Mexico, and East/West from Missouri to California. 'Density' is similar to most buffalograsses in water use demands, having excellent long term drought survival. 'Density' is adapted from sandy to heavier loam soil textures and from slightly acid to slightly alkaline soil pH.

TABLE 1

Leaf blade widths and lengths and texture class of selected buffalograss cultivars, measured under greenhouse conditions in Lebanon, OR, 2005.

| Variety | Clonal Sex | Canopy Height cm | Tillers per stolon node Number | Width, 4th youngest non-flowering stolon leaf mm | Leaf Sheath Length, non-flowering stolon cm |
|---|---|---|---|---|---|
| 'Density' | Female | 9.1 | 1.9 | 1.3 | 0.8 |
| '609' | Female | 17.8 | 1.5 | 1.4 | 1.0 |
| 'Prairie' | Female | 7.0 | 1.8 | 1.1 | 0.8 |

TABLE 2

Inflorescence and leaf characters of selected buffalograss cultivars, measured under greenhouse conditions in Lebanon, OR, 2005.

| Variety | Internode Length, 1st to 2nd stolon node cm | Internode Length, 2nd to 3rd stolon node cm | Anther length mm | Hair length, mouth of leaf sheath mm |
|---|---|---|---|---|
| 'Density' | 2.4 | 2.7 | Absent | 2.4 |
| '609' | 4.1 | 5.4 | Absent | 3.0 |
| 'Prairie' | 3.8 | 6.1 | Absent | 2.7 |

COMPLETE BOTANICAL DESCRIPTION OF THE VARIETY

Origin: 'Density' is a cultivar of a single female clone discovered under cultivated conditions in mowed roadside turf area near Houston, Tex.

Classification: *Buchloe dactyloides* (*Nutt*) *Engelm.,* diploid chromosome number.

Growth habit: 'Density' is a perennial female or pistilate clone that spreads by stolons and tillers and produces a fine textured turfgrass with a highly fibrous root system. The inflorescence of 'Density' is a female inflorescence terminating in a pistilate structure with purple stigmas and a burr-like structure.

Leaf blade: Rolled in the bud, mostly flat with some with a slightly concave surface.

Leaf blade pubescence: Few hairs on adaxial surface, none on abaxial surface.

Leaf sheath pubescence: Absent with few hairs on mouth of sheath, mean length: 'Density': 2.4 mm; 'Prairie': 2.7 mm; '609': 3.0 mm.

Leaf blade margin: Rough.

Leaf blade veins: Obscure.

Vegetative leaf, fourth youngest vegetative leaf:

*Blade length range.*—0.3 cm to 2.1 cm, mean length: 0.9 cm.

*Blade width mean.*—1.3 mm.

*Sheath length mean.*—0.8 cm.

Inflorescence characters:

*Culm total length, including floral area to node below flag leaf.*—8.1 cm.

*Culm width, stem thickness, base of floral area.*—0.5 mm.

*Number of burrs per flowering stalk.*—'Density': 2.0; '609': 3.0.

*Flag leaf length.*—3.5 cm.

*Flag leaf width.*—1.4 mm.

Stolon internode lengths:

*First internode to 2nd internode.*—'Density': 2.4 cm; '609': 4.1 cm; 'Prairie' U.S. Plant Pat. No. 7,539: 3.8 cm.

*Second internode to 3rd internode.*—'Density': 2.7 cm; '609': 5.4 cm; 'Prairie': 6.1 cm.

Mature plant height, including inflorescence: Density: 9.1; '609': 17.8 cm.

Color notations, vegetative characters, based on The R.H.S. Colour Chart (light quality, photoperiod, and general growth of the plants affect color notations):

*Leaf blade color adaxial leaf surface.*—146A yellow green.

*Stolon color.*—Small areas of 59A red purple, and 146B yellow green.

*Stigma.*—N79B purple.

Turf quality (rated 1–9, 9 best): 'Density' 7; '609': 6; 'Prairie': 5.

Turf color (rated 1–9, 9 best): 'Density' 7; '609': 7; 'Prairie': 5.

Turf density establishment rating (rated 1–9, 9 best): 'Density' 7; '609': 6; 'Prairie': 5.

Tiller production at stolon node rating: (rated 1–9, 9 best): 'Density' 7; '609': 6; 'Prairie': 5.

What is claimed is:

1. A new and distinct variety of female buffalograss plant, substantially as described and illustrated herein, characterized particularly by a female inflorescence, shorter plant canopy, and shorter stolon internode lengths.

* * * * *